United States Patent [19]

Sideman et al.

[11] Patent Number: 5,824,721
[45] Date of Patent: Oct. 20, 1998

[54] WATER SOLUBLE TRIAZOLE DERIVATIVE EMBOSSING INHIBITOR AND THE USE THEREOF

[75] Inventors: Carl E. Sideman, Lititz, Pa.; Donald M. Snyder, Saline, Mich.

[73] Assignee: Armstrong World Industries, Inc., Lancaster, Pa.

[21] Appl. No.: 658,511

[22] Filed: Jun. 10, 1996

[51] Int. Cl.$^6$ .................................................. C08D 249/16
[52] U.S. Cl. .......................................... 523/161; 548/260
[58] Field of Search .............................. 548/260; 523/161

[56] References Cited

U.S. PATENT DOCUMENTS

| | | | |
|---|---|---|---|
| 4,177,155 | 12/1979 | Popplewell | 252/49.3 |
| 4,464,276 | 8/1984 | Sung et al. | 252/42.7 |
| 4,683,071 | 7/1987 | Regenass | 548/260 |
| 4,791,206 | 12/1988 | O'Neil | 548/260 |
| 4,865,622 | 9/1989 | Sung | 44/63 |
| 5,169,435 | 12/1992 | Sherman et al. | 106/20 |
| 5,441,563 | 8/1995 | Sideman et al. | 106/224 |
| 5,585,228 | 12/1996 | Vishwakarma | 548/260 |

FOREIGN PATENT DOCUMENTS

| | | |
|---|---|---|
| 1466558 | 3/1977 | United Kingdom . |
| 1511593 | 5/1978 | United Kingdom . |
| 1514359 | 6/1978 | United Kingdom . |
| WO 96/07670 | 3/1996 | WIPO . |

*Primary Examiner*—Paul R. Michl

[57] ABSTRACT

This invention provides an aromatic or cycloaliphatic triazole-based chemical embossing inhibitor which is completely soluble in water and compatible with water-based printing inks for use in producing textured foamed plastic surfaces. The triazoles comprise a general class of mono- and multi-functional 1–N substituted aminomethyl derivatives which are rendered soluble in water by the presence of at least one polyethyleneoxide (PEO) oligomer chain, or polypropylene (PPO)-polyethyleneoxide copolymer oligomer chain or PPO/PEO/PPO triblock oligomer chain with a sufficiently high PEO/PPO ratio for water solubility. Preferably the triazole derivative has at least six polyethylene oxide monomer moieties per triazole moiety.

27 Claims, No Drawings

WATER SOLUBLE TRIAZOLE DERIVATIVE EMBOSSING INHIBITOR AND THE USE THEREOF

FIELD OF THE INVENTION

The invention relates to blowing agent inhibitors and their use. In particular, the invention is directed to water soluble triazole derivatives, and more particularly to water soluble triazole derivatives having a plurality of polyethylene oxide monomer moieties, preferably at least one polyethylene oxide (PEO) chain, which derivatives are effective blowing agent inhibitors.

BACKGROUND OF THE INVENTION

It is well known to those skilled in the art that foamed plastic surfaces may be textured by the process commonly referred to as "chemical embossing", wherein the surface of a foamable polymer composition is printed with an ink composition containing an agent which inhibits foaming in the printed areas when the surface is subsequently subjected to a heat treatment. The areas which have not been printed over thus expand normally on heating while expansion in the printed areas containing the inhibitor is retarded, resulting in a textured surface with depressions in those areas printed with the inhibited ink.

A wide range of compounds have been claimed to act as inhibitors for chemical embossing of floor and wall covering surfaces. Carboxylic acid anhydrides such as trimellitic anhydride (TMA), disclosed in Nairn et al. U.S. Pat. No. 3,293,094, being among the most commonly used industrially. However, compounds such as TMA, while suitable for solvent-based printing inks, are hydrolytically unstable and thus are not readily usable in the aqueous ink formulations rapidly gaining in importance in large scale printing operations due to environmental concerns over VOC emission from solvent-based inks.

Triazole compounds such as benzotriazole (BTA) and tolyltriazole (TTA) are also widely used in solvent-based inks for chemical embossing. These compounds do not hydrolyze to inactive form on contact with water as do carboxylic acid anhydrides like TMA. However their use in aqueous ink systems is hindered by a lack of substantial water solubility.

The excellent embossing characteristics, stability and low toxicity of the aromatic triazoles have prompted considerable research into ways that these compounds could be successfully adapted to aqueous ink systems. The prior art, specifically Hamilton U.S. Pat. No. 4,083,907 and Hamilton U.S. Pat. No. 4,191,581, has established that sufficient BTA or aminotriazole for acceptable embossing can be solubilized into an aqueous ink by addition of a water soluble alcohol and buffering agents to raise the pH of the ink formulation to between 8–12.

Certain carboxylic acids, acid anhydrides and acid halides have also been claimed to act as foam-expansion inhibitors in aqueous ink formulations where the acidic species have been neutralized and the formulation pH adjusted to the same 8–12 range (Brixius U.S. Pat. No. 4,369,065 and Brixius U.S. Pat. No. 4,421,561).

Benzotriazole and other inhibitor species have also been solubilized in alcohol-containing aqueous inks where the system pH is in the acidic range from 3–5 (Sherman et al. U.S. Pat. No. 5,169,435).

Modified aromatic triazole derivatives have also been cited as foam-expansion inhibitors. These compounds are substituted on the 1–N of the triazole ring with dialkylaminomethyl groups of varying structure and are claimed to be easily incorporated into aqueous inks which contain alcohols or other water soluble organic solvents, and do not require the use of a pH regulator (Hauser et al. U.S. Pat. No. 4,407,882). Compounds of this general structure in which the alkyl groups of the aminomethyl substituent are simple hydrocarbons (D'Errico U.S. Pat. No. 4,522,785) and perfluoroalkyls (Clark et al. U.S. Pat. No. 4,788,292) have also been claimed as corrosion inhibitors.

Insoluble aromatic and cycloaliphatic azole-based chemical embossing inhibitors are disclosed in Sideman et al. U.S. Pat. No. 5,441,563 and Remar et al. U.S. patent application Ser. No. 515,110, filed Aug. 14, 1995.

In order to enhance the solubility of such derivatives in a wide range of functional fluids of varying polarity, a dialkylaminomethyl benzotriazole corrosion inhibitor has also been claimed (Poplewell et al. U.K. Patent No. 1,466,558) wherein one of the aminomethyl alkyl groups may be a short polyethyleneoxide chain of 1–4 repeat units.

As the triazole-based foam-expansion inhibitors established in the patent literature to date are not soluble in water unless alcohols or other suitably water-miscible organic co-solvents are also present, there continues to exist a need in the art for a water-soluble triazole-based inhibitor which does not require such co-solvents, in order to reduce VOC emissions during the printing and drying process.

SUMMARY OF THE INVENTION

The dialkylaminomethyltriazole derivatives cited previously as foam-expansion inhibitors and corrosion inhibitors are readily prepared by the known reaction of the starting triazole with a secondary amine and formaldehyde in a suitable solvent at varying temperatures. It has also been established that if the alkylamine which is to be incorporated as the aminomethyl group is primary rather than secondary, and a suitable ratio of triazole to amine is used, the product will have two methyltriazoyl groups on the original amine nitrogen (Frankenfeld et al. U.S. Pat. No. 5,076,946).

In the present invention, by using primary or secondary mono- or diamines in which at least one of the substituents is a polyethylene oxide (PEO) oligomer of sufficient molecular weight, or a polypropylene oxide (PPO)/PEO/PPO triblock oligomer with a sufficiently high PEO/PPO ratio, the resulting aminomethyltriazole will be completely soluble in water without the need for alcohol or other water-miscible organic co-solvents. The PPO/PEO/PPO triblock oligomer has the general formula $PPO_xPEO_yPPO_z$, where x, y and z are positive integers.

The number of PEO repeat units required to confer water solubility to the molecule is related to the number of aminomethyltriazole moieties attached to the molecule. The triazole derivatives of the present invention will be soluble in water if the ratio of polyethylene oxide monomer moieties to triazole moieties is at least six and preferably at least eight. The chemical embossing inhibitors embodied in this invention have the advantage that they are inherently soluble in water and can be completely dissolved in aqueous ink formulations without the necessity of added alcohols or other water-soluble co-solvents, or surfactants. However, such co-solvents or surfactants can be added without destroying the present invention.

Accordingly, it is the object of the present invention to provide a printing ink composition for the production of textured foamed surface, which composition comprises a resin, water, and as inhibitor for preventing the foaming of a foamable material containing a blowing agent, a PEO or PEO/PPO substituted triazole derivative of the formula

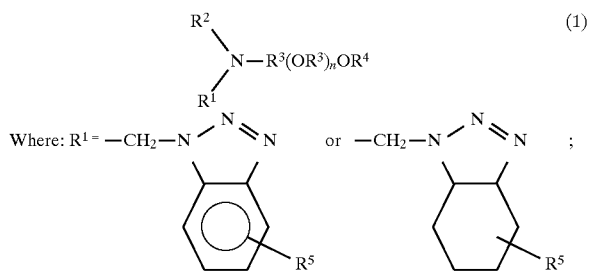

$R^2 = -(C_1-C_4)$ alkyl, $-(CH_2CH_2O)_mCH_3$, $-(CH_2CH_2O)_mCH_2CH_3$, or $-R^1$;

$R^3 = -CH_2CH_2-$, $-CH(R^6)CH_2-$, or $-CH_2CH(R^6)-$;

$R^4 = -(C_1-C_4)$ alkyl, or $$-R^3-N\begin{matrix}R^2\\ \\R^1\end{matrix} \quad ;$$

$R^5 = -H$ or $-(C_1-C_4)$ alkyl;
$R^6 = -(C_1-C_4)$ alkyl;
n=3–45;
m=1–6; and
Each of $R^1$, $R^2$, $R^3$, $R^5$, and $R^6$ may be the same or different.

$R^3$ is preferably $-CH_2CH_2-$, $-CH(CH_3)CH_2-$, or $-CH_2CH(CH_3)-$. $R^5$ is preferably $-H$ or $-CH_3$.

When $R^4$ is $-R^3N(R^1)$alkyl, n is preferably 10 to 25. When $R^4$ is $-R^3N(R^1)_2$, n is preferably 20 to 45, more preferably 20 to 35, and most preferably 20 to 30.

When $R^2$ is $R^1$ and $R^4$ is $-(C_1-C_4)$alkyl, n is preferably 10 to 30, and more preferably 15 to 25. When $R^2$ is not $R^1$ and $R^4$ is $-(C_1-C_4)$ alkyl, n is preferably 5 to 25, and more preferably 7 to 25.

Another object of the invention is to provide a water soluble triazole derivative which includes a plurality of polyethylene oxide monomer moieties, preferably a ratio of polyethylene oxide monomer moieties to triazole moieties of at least six, and more preferably a ratio of polyethylene oxide monomer moieties to triazole moieties of at least eight.

A further object of the invention is to provide a PEO or PEO/PPO substituted triazole derivative of Formula (1), except n=5–45.

A still further object of the invention is to provide a method of embossing a heat-foamable resinous material by applying the printing ink composition of the present invention to selected areas of the surface of a heat-foamable resinous material, which material contains a blowing agent, and subsequently heating the material to at least the decomposition temperature of the blowing agent.

DETAILED DESCRIPTION OF THE INVENTION

Structures for some representative examples of the water soluble triazole derivatives of the present invention are shown in the following Tables I and II in which the substituents of Formula (1) are identified. $R^1$ is identified as aromatic to indicate the first moiety set forth for $R^1$, supra, or cyclohexyl to indicate the second moiety set forth for $R^1$, supra. $R^2$ is sometimes identified in the same manner. The parenthetical numbers following the moieties of $R^3$ indicate the average number of the $OR^3$ moieties in the compound. The average number of polyethylene oxide monomer moieties and polypropylene oxide monomer moieties is one greater than n.

TABLE I

Mono- and Vicinal Di-substituted Derivatives

| Cmpd | $R^1$ | $R^5$ | $R^4$ | $R^2$ | $R^3$ | n |
|---|---|---|---|---|---|---|
| 1 | Aromatic | $-CH_3$ | $-CH_3$ | $-CH_2CH_2OCH_3$ | $-CH_2CH_2-$ | 3–9 |
| 2 | Aromatic | $-CH_3$ | $-CH_3$ | Aromatic | $-CH_2CH_2-$ (19),<br>$-CH(CH_3)CH_2-/-CH_2CH(CH_3)-$ (4) | 22 |
| 3 | Aromatic | $-CH_3$ | $-CH_3$ | Aromatic | $-CH_2CH_2-$ (13),<br>$-CH(CH_3)CH_2-/-CH_2CH(CH_3)-$ (3) | 15 |
| 4 | Aromatic | $-H$ | $-CH_3$ | Aromatic | $-CH_2CH_2-$ (13),<br>$-CH(CH_3)CH_2-/-CH_2CH(CH_3)-$ (3) | 15 |
| 5 | Cyclohexyl | $-CH_3$ | $-CH_3$ | Aromatic | $-CH_2CH_2-$ (13),<br>$-CH(CH_3)CH_2-/-CH_2CH(CH_3)-$ (3) | 15 |
| 6 | Aromatic | $-CH_3$ | $-CH_3$ | $-CH_3$ | $-CH_2CH_2-$ (13),<br>$-CH(CH_3)CH_2-/-CH_2CH(CH_2)-$ (3) | 15 |

TABLE II

Symmetrical Di- and Tetra-substituted Derivatives

| Cmpd | $R^1$ | $R^5$ | $R^2$ | $R^4$ | $R^3$ | n |
|---|---|---|---|---|---|---|
| 7 | Aromatic | $-CH_3$ | $-CH_3$ | $-CH_2CH(CH_3)NR^1R^2$ | $-CH_2CH_2-$ (15.5),<br>$-CH(CH_3)CH_2-/-CH_2CH(CH_3)-$ (3.5) | 18 |
| 8 | Aromatic | $-H$ | $-CH_3$ | $-CH_2CH(CH_3)NR^1R^2$ | $-CH_2CH_2-$ (15.5),<br>$-CH(CH_3)CH_2-/-CH_2CH(CH_3)-$ (3.5) | 18 |

TABLE II-continued

Symmetrical Di- and Tetra-substituted Derivatives

| Cmpd | $R^1$ | $R^5$ | $R^2$ | $R^4$ | $R^3$ | n |
|------|-------|-------|-------|-------|-------|---|
| 9 | Cyclohexyl | —$CH_3$ | —$CH_3$ | —$CH_2CH(CH_3)NR^1R^2$ | —$CH_2CH_2$— (15.5)<br>—$CH(CH_3)CH_2$—/—$CH_2CH(CH_3)$— (3.5) | 18 |
| 10 | Aromatic | —$CH_3$ | Aromatic | —$CH_2CH(CH_3)NR^1R^2$ | —$CH_2CH_2$— (39.5)<br>—$CH(CH_3)CH_2$—/—$CH_2CH(CH_3)$— (3.5) | 42 |
| 11 | Aromatic | —H | Aromatic | —$CH_2CH(CH_3)NR^1R^2$ | —$CH_2CH_2$— (39.5)<br>—$CH(CH_3)CH_2$—/—$CH_2CH(CH_3)$— (3.5) | 42 |
| 12 | Cyclohexyl | —$CH_3$ | Cyclohexyl | —$CH_2CH(CH_3)NR^1R^2$ | —$CH_2CH_2$— (39.5)<br>—$CH(CH_3)CH_2$—/—$CH_2CH(CH_3)$— (3.5) | 42 |

For acceptable processing, it is advantageous to use 5 to 25 parts by weight of the polyalkyleneoxide-derivatized aminomethyltriazoles in the aqueous printing ink composition. Those skilled in the art will recognize that a very wide range of printing ink compositions exist with varying combinations of solubilized and/or dispersible binders, pigments, and rheology-control additives. The pigments are optional, since it may be desirable to use a colorless, inhibitor containing printing ink. The water-soluble triazoles of the present invention are potentially useful in many other aqueous ink formulations not specifically outlined in the Examples as to their exact composition.

Those skilled in the art will also recognize that varying amounts of water will be required to adjust the viscosity of the ink composition to a range suitable for typical rotogravure printing. Other methods of printing the ink composition onto the foamable plastic surface, such as screen printing, relief printing, or planographic printing, may also be used with these ink compositions.

Although this invention is primarily concerned with polyvinylchloride-based plastisol compositions thermally blown with azodicarbonamide as the printing substrate, there likewise exists a wide range of thermoplastic resins which can be thermally foamed with azodicarbonamide and thus are potential substrates for aqueous inhibitor printing ink compositions of the type claimed. Such other compositions include polyvinylacetate, copolymers of vinyl chloride and vinyl acetate, polyacrylate, polymethacrylate, polyethylene, polystyrene, butadiene/styrene copolymers, butadiene/acrylonitrile copolymers, and natural or synthetic rubbers.

The specific combinations of PVC, other thermoplastic resins, filler, stabilizers, liquid plasticizer and chemical blowing agent that make up a typical foamable plastisol substrate vary widely within certain limits and those skilled in the art can reasonably anticipate systems which would be encompassed by the scope of this invention.

The invention is illustrated by the following examples related to synthesis of the water-soluble triazole derivatives, preparation of the aqueous printing ink formulations and demonstration of the chemical embossing behavior of the claimed compounds. Unless otherwise stated, all amounts and percentages given in the Examples are on a weight basis.

EXAMPLE 1

Synthesis of Compound 1

1-N-[(2-Methoxyethylmethoxypolyethyleneoxy)aminomethyl]tolyltriazole

Sixteen and one-half parts of commercial tolyltriazole (TT100, an isomer mixture from PMC Specialties) and 50.4 parts of the PEO-substituted secondary amine (laboratory prepared) were combined in 150 parts methanol and cooled to zero degrees Centigrade. While holding the reaction mixture at this temperature, 10.1 parts of commercial 37% aqueous formaldehyde solution was added slowly over several hours with continual agitation. The reaction mixture was allowed to warm to ambient temperature and worked up after 18 hours by removing the solvent under moderate heat/vacuum. The resulting oil was then vacuum stripped at higher temperature to remove any residual water, unreacted formaldehyde or other volatiles. The final product was 67.1 parts (quantitative yield) of a clear, mobile reddish oil which was identified by standard spectroscopic techniques as the expected Compound 1,1-N-[(2-methoxyethylmethoxypolyethyleneoxy)aminomethyl]tolyltriazole. The compound was found to be completely miscible with water in all proportions.

EXAMPLE 2

Synthesis of Compound 2

N,N-Bis(1-N-Tolytriazoylmethyl)polyethylene-Co-Polypropyleneoxyamine

Twenty-six and seven-tenths parts of commercial tolyltriazole and 100.0 parts of the PEO/PPO-substituted primary amine (JEFFAMINE M1000 from Texaco Chemical Co.) were combined in 150 parts methanol and cooled to zero degrees Centigrade. While holding the reaction mixture at this temperature, 16.3 parts of commercial 37% aqueous formaldehyde solution was added slowly over several hours with continual agitation. The reaction mixture was allowed to warm to ambient temperature and worked up after 18 hours by removing the solvent under moderate heat/vacuum. The resulting oil was then vacuum stripped at higher temperature to remove any residual water, unreacted formaldehyde or other volatiles. The final product was 128.7 parts (quantitative yield) of a clear, mobile reddish oil which was identified by standard spectroscopic techniques as the expected Compound 2, N,N-bis(1-N-tolytriazoylmethyl)polyethylene-co-polypropyleneoxyamine. The compound was found to be completely miscible with water in all proportions.

EXAMPLE 3

Synthesis of Compound 3

N,N-Bis(1-N-Tolytriazoylmethyl)polyethylene-Co-Polypropyleneoxyamine

Thirty-seven and three-tenths parts of commercial tolyltriazole and 100.0 parts of the PEO/PPO-substituted primary amine (JEFFAMINE M715 from Texaco Chemical Co.) were combined in 150 parts methanol and cooled to zero degrees Centigrade. While holding the reaction mixture at this temperature, 22.7 parts of commercial 37% aqueous formaldehyde solution was added slowly over several hours with continual agitation. The reaction mixture was allowed to warm to ambient temperature and worked up after 18 hours by removing the solvent under moderate heat/vacuum. The resulting oil was then vacuum stripped at higher temperature to remove any residual water, unreacted formaldehyde or other volatiles. The final product was 163.9 parts (quantitative yield) of a clear, mobile reddish oil which was identified by standard spectroscopic techniques as the expected Compound 3. This compound differed from Compound 2 only in the number of repeat units in the PEO/PPO chain and was also found to be completely miscible with water in all proportions.

EXAMPLE 4

Synthesis of Compound 4

N,N-Bis(1-N-Benzotriazoylmethyl)polyethylene-Co-Polypropyleneoxyamine

Twenty-three and eight tenths parts of commercial benzotriazole and 71.5 parts of the PEO/PPO-substituted primary amine (JEFFAMINE M715 from Texaco Chemical Co.) were combined in 100 parts of methanol and cooled to zero degrees Centigrade. While holding the reaction mixture at this temperature, 16.2 parts of commercial 37% aqueous formaldehyde solution was added slowly over several hours with continual agitation. The reaction mixture was allowed to warm to ambient temperature and worked up after 18 hours by removing the solvent under moderate heat/vacuum. The resulting oil was then vacuum stripped at higher temperature to remove any residual water, unreacted formaldehyde or other volatiles. The final product was 97.0 parts (99.3% yield) of a clear, mobile oil, slightly yellow in color, which was identified by standard spectroscopic techniques as the expected Compound 4, N,N-bis(1-N-benzotriazoylmethyl)polyethylene-co-polypropyleneoxyamine. The compound was found to be completely miscible with water in all proportions.

EXAMPLE 5

Synthesis of Compound 5

N,N-Bis(1-N-Methylcyclohexyltriazoylmethyl) polyethylene-Co-Polypropylene-Oxyamine Forty and four-tenths parts of hydrogenated tolyltriazole (Cobratec 911 from PMC Specialties) and 103.8 parts of the PEO/PPO-substituted primary amine (JEFFAMINE M715 from Texaco Chemical Co.) were combined in 150 parts of methanol and cooled to zero degrees Centigrade. While holding the reaction mixture at this temperature, 23.5 parts of commercial 37% aqueous formaldehyde solution was added slowly over several hours with continual agitation. The reaction mixture was allowed to warm to ambient temperature and worked up after 18 hours by removing the solvent under moderate heat/vacuum. The resulting oil was then vacuum stripped at higher temperature to remove any residual water, unreacted formaldehyde or other volatiles. The final product was 146.8 parts (quantitative yield) of a clear, mobile oil, slightly yellow in color, which was identified by standard spectroscopic techniques as the expected Compound 5, N,N-bis(1-N-methylcyclohexyltriazoylmethyl)polyethylene-co-polypropylene-oxyamine. The compound was found to be completely miscible with water in all proportions.

EXAMPLE 6

Synthesis of Compound 10

N,N,N',N'-Tetra(1-N-Tolyltriazoylmethyl) polyethylene-Co-PolypropyleneOxydiamine Twenty-six and seven-tenths parts of commercial tolyltriazole and 100.0 parts of the PEO/PPO-substituted primary diamine (JEFFAMINE ED-2001 from Texaco Chemical Co.) were combined in 150 parts of methanol and cooled to zero degrees Centigrade. While holding the reaction mixture at this temperature, 16.3 parts of commercial 37% aqueous formaldehyde solution was added slowly over several hours with continual agitation. The reaction mixture was allowed to warm to ambient temperature and worked up after 18 hours by removing the solvent under moderate heat/vacuum. The resulting oil was then vacuum stripped at higher temperature to remove any residual water, unreacted formaldehyde or other volatiles. The final product was 128.6 parts (99.6% yield) of a clear, mobile oil, slightly yellow in color, which was identified by standard spectroscopic techniques as the expected Compound 10, N,N,N',N'-tetra(1-N-tolyltriazoylmethyl)polyethylene-co-polypropyleneoxydiamine. The compound was found to be completely miscible with water in all proportions.

EXAMPLES 7 TO 10

Preparation and Testing of Inks (10% Concentration)

Four inks were made using the compounds from Examples 1, 2, 3 and 6. These compounds were added directly to Sicpa's anionic water-based ink extender 694550 at a concentration of 10% active inhibitor. These compounds readily solubilized into the ink extender without any adverse reactions. Two controls were evaluated at the same time (i.e., 10% Benzotriazole and 8% Trimellitic anhydride) in a solvent-base extender.

All five inks were printed into 9 mils of an expandable plastisol coated on flooring felt and on 7 mils of an expandable plastisol coated onto a saturated glass mat. The plastisol formulation coated on the flooring felt was 100 parts by weight PVC resin, 50 parts plasticizer, 30 parts limestone filler, 7.0 parts titanium dioxide pigment, 3.0 parts mineral spirits viscosity modifier, 2.1 parts stabilizers, 2.0 parts azodicarbonamide blowing agent and 0.6 parts zinc oxide blowing agent activator. The printing was done on a flat-bed gravure proof press using a 100 line screen step-wedge engraved plate. The steps ranged from a deep shadow tone to a shallow highlight tone.

The printed samples were coated with 10 mils of a clear plastisol wearlayer, and fused and expanded in a Werner Mathis oven. The clear wearlayer was 100 parts by weight PVC resin, 40 parts plasticizer, 4.0 parts stabilizers and 4.0 parts mineral spirits. The felt backed structure was heated for 1.3±0.1 minutes at an air temperature of 201°±1° C. to a blow ratio of about 2.8 to 1.

The plastisol formulation coated on the glass mat was 100 parts by weight PVC resin, 55 parts plasticizer, 30 parts limestone filler, 5.0 parts titanium dioxide pigment, 3.0 parts mineral spirits viscosity modifier, 2.0 parts azodicarbonamide blowing agent and 0.5 parts zinc oxide blowing agent activator. The printing was done on a flat-bed gravure proof press using a 100 line screen step-wedge engraved plate. The steps ranged from a deep shadow tone to a shallow highlight tone.

The printed samples were coated with 10 mils of a clear plastisol wearlayer, and fused and expanded in a Werner Mathis oven. The clear wearlayer was 100 parts by weight PVC resin, 50 parts plasticizer and 2.0 parts stabilizers. The glass backed structure was heated for 1.9±0.1 minutes at an air temperature of 185°±2° C. to a blow ratio of about 2.0 to 1.

The thickness of the printed areas (i.e., restricted area) was measured in mils and compared to the thickness of the unprinted expanded surrounding areas. This difference is reported as the depth of chemical embossing and is shown in Table III.

TABLE III

| INHIBITOR | WEIGHT PERCENT OF COMPOUND IN INK | DEPTH OF EMBOSSING FOR FELT STRUCTURE in mils | DEPTH OF EMBOSSING FOR GLASS STRUCTURE in mils |
|---|---|---|---|
| Example 7 (Compound 1) | 10% | 5.7 | 4.7 |
| Example 8 (Compound 2) | 10% | 4.4 | 2.9 |
| Example 9 (Compound 3) | 10% | 5.5 | 3.9 |
| Example 10 (Compound 10) | 10% | 3.0 | 3.2 |
| BTA | 10% | 11.8 | 3.5 |
| TMA | 8% | 8.6 | 5.9 |

EXAMPLES 11 TO 13

Preparation and Testing of Inks (15% Concentration)

The following three inks were made using compounds from Examples 3, 4 and 5. They were mixed with Sicpa's anionic water-based ink extender 694556 at a concentration of 15% by weight, without any problems. A 10% Benzotriazole solvent-based ink control was used for this evaluation. These inks were printed on the same felt backed and glass backed structures used in Table III and evaluated by the same method for the depth of chemical embossing (see Table IV).

TABLE IV

| INHIBITOR | WEIGHT PERCENT OF COMPOUND IN INK | DEPTH OF EMBOSSING FOR FELT STRUCTURE in mils | DEPTH OF EMBOSSING FOR GLASS STRUCTURE in mils |
|---|---|---|---|
| Example 11 (Compound 3) | 15% | 6.8 | 4.9 |
| Example 12 (Compound 4) | 15% | 8.6 | 4.8 |
| Example 13 (Compound 5) | 15% | 8.9 | 4.3 |
| BTA | 10% | 11.7 | 3.9 |

EXAMPLES 14 TO 16

Preparation and Testing of Compound 3 Inks (10%, 15% & 20% Concentration)

Example 3 (Compound 3) was evaluated at three concentrations to see if the depth of chemical embossing would improve with higher concentrations. This compound was added to Siopa's anionic water-based ink extender 694556 at three concentrations (i.e., 10%, 15% and 20%). A 10% Benzotriazole solvent-based ink control was used on the same felt backed structure coated with 9 mils of expandable plastisol The same method used previously was used to evaluate the chemical embossing depth (see Table V).

TABLE V

| INHIBITOR | WEIGHT PERCENT OF COMPOUND IN INK | DEPTH OF EMBOSSING FOR FELT STRUCTURE in mils |
|---|---|---|
| Example 14 (Compound 3) | 10% | 5.7 |
| Example 15 (Compound 3) | 15% | 8.1 |
| Example 16 (Compound 3) | 20% | 10.0 |
| BTA | 10% | 13.1 |

We claim:

1. A compound having the formula

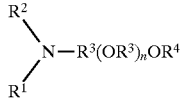

Where: $R^1 =$  or

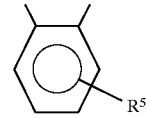

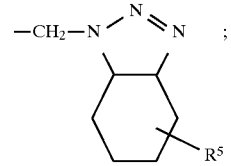

$R^2 = -(C_1-C_4)$ alkyl, $-(CH_2CH_2O)_m CH_3$, $-(CH_2CH_2O)_m CH_2CH_3$, or $-R^1$;

$R^3 = -CH_2CH_2-$, $-CH(R^6)CH_2-$, or $-CH_2CH(R^6)-$;

$R^4 = -(C_1-C_4)$ alkyl, or

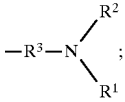

$R^5 = -H$ or $-(C_1-C_4)$ alkyl;

$R^6 = -(C_1-C_4)$ alkyl;

n=5–45;

m=1–6; and

Each of $R^1$, $R^2$, $R^3$, $R^5$, and $R^6$ may be the same or different.

2. The compound of claim 1 wherein the $R^1$ is aromatic.

3. The compound of claim 1 wherein the compound is mono-triazole substituted.

4. The compound of claim 1 wherein the compound is di-triazole substituted.

5. The compound of claim 1 wherein n=10 to 25 and $R^4$ is a mono-triazole substituted amino moiety.

6. The compound of claim 1 wherein n=20 to 45 and $R^4$ is a di-triazole substituted amino moiety.

7. The compound of claim 1 wherein n=5 to 25, $R^4$ is an alkyl moiety, and $R^2$ is other than a triazole moiety.

8. A printing ink composition comprising a thermoplastic resin, water and the compound of claim 1.

9. A printing ink composition comprising a thermoplastic resin, water and an inhibitor, the thermoplastic resin being a blend of a polyvinylchloride polymer and an acrylic polymer, and the inhibitor having the following formula

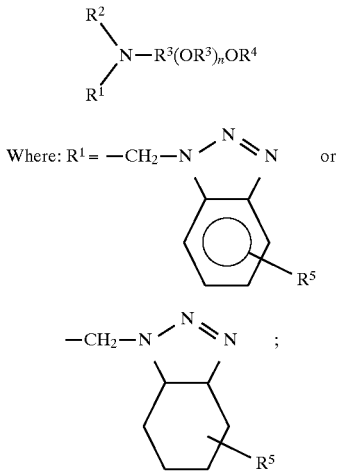

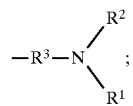

$R^2$=—($C_1$-$C_4$) alkyl, —$(CH_2CH_2O)_mCH_3$, —$(CH_2CH_2O)_mCH_2CH_3$, or —$R^1$;

$R^3$=—$CH_2CH_2$—, —$CH(R^6)CH_2$—, or —$CH_2CH(R^6)$—;

$R^4$=—($C_1$-$C_4$) alkyl, or $R^5$=—H or —($C_1$-$C_4$) alkyl;
$R^6$=—($C_1$-$C_4$) alkyl;
n=3–45;
m=1–6; and
each of $R^1$, $R^2$, $R^3$, $R^5$, and $R^6$ may be the same or different.

10. The composition of claim 9 wherein the $R^1$ is aromatic.

11. The composition of claim 9 wherein the inhibitor is mono-triazole substituted.

12. The composition of claim 9 wherein the inhibitor is di-triazole substituted.

13. The composition of claim 9 wherein n=10 to 25 and $R^4$ is a mono-triazole substituted amino moiety.

14. The composition of claim 9 wherein n=20 to 45 and $R^4$ is a di-triazole substituted amino moiety.

15. The composition of claim 9 wherein n=3 to 25, $R^4$ is an alkyl moiety, and $R^2$ is other than a triazole moiety.

16. The method of claim 15, wherein the heat-foamable material is selected from the group consisting of polyvinylchloride, polyvinylacetate, copolymers of vinyl chloride and vinyl acetate, polyacrylate, polymethacrylate, polyethylene, polystyrene, butadiene/styrene copolymers, butadiene/acrylonitrile copolymers, and natural or synthetic rubbers.

17. The structure obtained according to claim 15.

18. A method of embossing a heat-foamable, resinous material comprising applying the printing ink composition comprising a thermoplastic resin, water and an inhibitor to selected areas of the surface of the heat-foamable material, which heat-foamable material contains a blowing agent, and heating the heat-foamable material to at least the decomposition temperature of the blowing agent, the inhibitor having the following formula

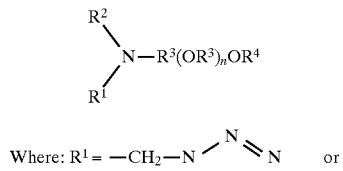

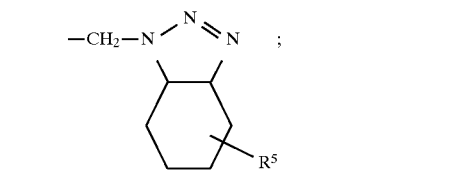

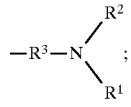

$R^2$=—($C_1$-$C_4$) alkyl, —$(CH_2CH_2O)_mCH_3$, —$(CH_2CH_2O)_mCH_2CH_3$, or —$R^1$;

$R^3$=—$CH_2CH_2$—, —$CH(R^6)CH_2$—, or —$CH_2CH(R^6)$—;

$R^4$=—($C_1$-$C_4$) alkyl, or $R^5$=—H or —($C_1$-$C_4$) alkyl;
$R^6$=—($C_1$-$C_4$) alkyl;
n=10–30 when $R^2$ is $R^1$ and $R^4$ is —($C_1$-$C_4$)alkyl, 7–25 when $R^2$ is not $R^1$ and $R^4$ is —($C_1$-$C_4$)alkyl, and 20–45 when $R^4$ is —$R^3N(R^1)$alkyl;
m=1–6; and
each of $R^1$, $R^2$, $R^3$, $R^5$ and $R^6$ may be the same or different.

19. A method of embossing a heat-foamable, resinous material comprising applying the printing ink composition comprising a thermoplastic resin, water and an inhibitor to selected areas of the surface of the heat-foamable material, which heat-foamable material contains a blowing agent, and heating the heat-foamable material to at least the decomposition temperature of the blowing agent, the inhibitor having the following formula

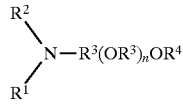

-continued

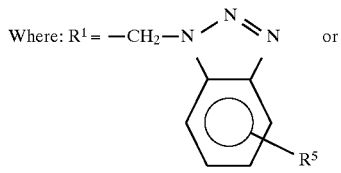

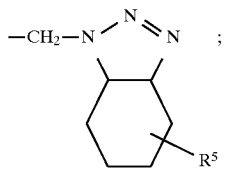

$R^2 = -(C_1-C_4)$ alkyl, $-(CH_2CH_2O)_mCH_3$, $-(CH_2CH_2O)_mCH_2CH_3$, or $-R^1$;

$R^3 = -CH_2CH_2-$, $-CH(R^6)CH_2-$, or $-CH_2CH(R^6)-$;

$R^4 = -(C_1-C_4)$ alkyl, or

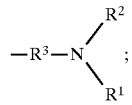

$R^5 = -H$ or $-(C_1-C_4)$ alkyl;

$R^6 = -(C_1-C_4)$ alkyl;

n=5–45;

m=1–6;

the ratio of polyethylene oxide monomer moieties to triazole moieties is at least six; and each of $R^1$, $R^2$, $R^3$, $R^5$ and $R^6$ may be the same or different.

20. A compound having the formula

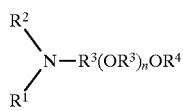

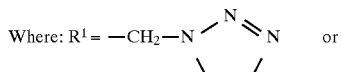

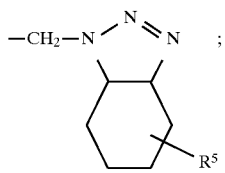

$R^2 = -(C_1-C_4)$ alkyl, $-(CH_2CH_2O)_mCH_3$, $-(CH_2CH_2O)_mCH_2CH_3$, or $-R^1$;

$R^3 = -CH_2CH_2-$, $-CH(R^6)CH_2-$, or $-CH_2CH(R^6)-$;

$R^4 = -(C_1-C_4)$ alkyl, or

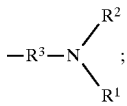

$R^5 = -H$ or $-(C_1-C_4)$ alkyl;

$R^6 = -(C_1-C_4)$ alkyl;

n=10–30 when $R^2$ is $R^1$ and $R^4$ is $-(C_1-C_4)$alkyl, 7–25 when $R^2$ is not $R^1$ and $R^4$ is $-(C_1-C_4)$alkyl, and 20–45 when $R^4$ is $-R^3N(R^1)$alkyl;

m=1–6; and each of $R^1$, $R^2$, $R^3$, $R^5$ and $R^6$ may be the same or different.

21. A compound having the formula

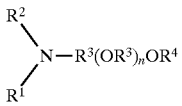

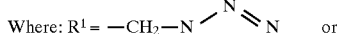

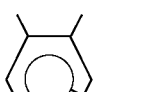

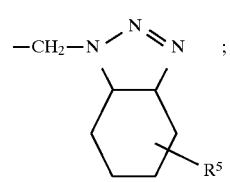

$R^2 = -(C_1-C_4)$ alkyl, $-(CH_2CH_2O)_mCH_3$, $-(CH_2CH_2O)_mCH_2CH_3$, or $-R^1$;

$R^3 = -CH_2CH_2-$, $-CH(R^6)CH_2-$, or $-CH_2CH(R^6)-$;

$R^4 = -(C_1-C_4)$ alkyl, or

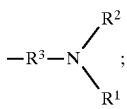

$R^5 = -H$ or $-(C_1-C_4)$ alkyl;

$R^6 = -(C_1-C_4)$ alkyl;

n=5–45;

m=1–6;

the ratio of polyethylene oxide monomer moieties to triazole moieties is at least six; and each of $R^1$, $R^2$, $R^3$, $R^5$ and $R^6$ may be the same or different.

22. The compound of claim 21 wherein the ratio of polyethylene oxide monomer moieties to triazole moieties is at least 8.

23. A compound having the formula

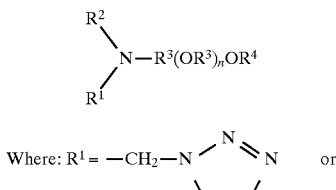

Where: $R^1 = $ 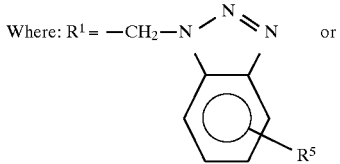 or

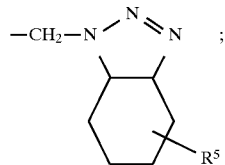 ;

$R^2 = -(C_1-C_4)$ alkyl, $-(CH_2CH_2O)_m CH_3$, $-(CH_2CH_2O)_m CH_2CH_3$, or $-R^1$;

$R^3 = -CH_2CH_2-$, $-CH(R^6)CH_2-$, or $-CH_2CH(R^6)-$;

$R^4 = $ 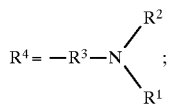 ;

$R^5 = -H$ or $-(C_1-C_4)$ alkyl;

$R^6 = -(C_1-C_4)$ alkyl;

n=3–45;

m=1–6; and each of $R^1$, $R^2$, $R^3$, $R^5$, and $R^6$ may be the same or different.

24. A printing ink composition comprising a thermoplastic resin, water and an inhibitor having the following formula

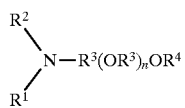

Where: $R^1 = $ 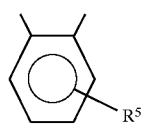 or

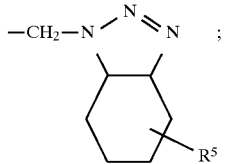 ;

$R^2 = -(C_1-C_4)$ alkyl, $-(CH_2CH_2O)_m CH_3$, $-(CH_2CH_2O)_m CH_2CH_3$, or $-R^1$;

$R^3 = -CH_2CH_2-$, $-CH(R^6)CH_2-$, or $-CH_2CH(R^6)-$;

$R^4 = -(C_1-C_4)$ alkyl, or

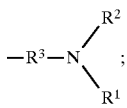 ;

$R^5 = -H$ or $-(C_1-C_4)$ alkyl;

$R^6 = -(C_1-C_4)$ alkyl;

n=5–45;

m=1–6;

the ratio of polyethylene oxide monomer moieties to triazole moieties is at least six; and each of $R^1$, $R^2$, $R^3$, $R^5$ and $R^6$ may be the same or different.

25. The printing ink composition of claim 24 wherein the ratio of polyethylene oxide monomer moieties to triazole moieties is at least 8.

26. The printing ink composition of claim 8 wherein n=10–30 when $R^2$ is $R^1$ and $R^4$ is $-(C_1-C_4)$alkyl, n=7–25 when $R^2$ is not $R^1$ and $R^4$ is $-(C_1-C_4)$alkyl, and n=20–45 when $R^4$ is $-R^3-N(R^1)$alkyl.

27. The printing ink composition of claim 8 wherein $R^4$ is $-R^3-N(R^1)R^2$.

* * * * *